United States Patent
Ruff et al.

(10) Patent No.: US 8,260,397 B2
(45) Date of Patent: Sep. 4, 2012

(54) MAGNETIC RESONANCE METHOD AND APPARATUS FOR DETERMINING A KIDNEY FUNCTION PARAMETER

(75) Inventors: Jan Ruff, Munich (DE); Stefan Roell, West Chester, PA (US); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 437 days.

(21) Appl. No.: 12/572,374

(22) Filed: Oct. 2, 2009

(65) Prior Publication Data

US 2010/0087726 A1   Apr. 8, 2010

(30) Foreign Application Priority Data

Oct. 2, 2008   (DE) .................. 10 2008 050 347

(51) Int. Cl.
*A61B 5/05* (2006.01)
(52) U.S. Cl. ........ 600/410; 600/407; 600/411; 600/412; 600/413; 600/414; 600/415; 600/416; 600/417; 600/418; 600/419; 600/420; 600/421; 600/422; 600/423; 324/307; 324/308; 324/309
(58) Field of Classification Search .................. 600/407, 600/410–423; 324/300, 307–309
See application file for complete search history.

(56) References Cited

U.S. PATENT DOCUMENTS

| | | | | |
|---|---|---|---|---|
| 3,124,136 A * | 3/1964 | Usher | .............. | 606/213 |
| 5,199,436 A * | 4/1993 | Pompei et al. | .............. | 600/474 |
| 5,287,273 A * | 2/1994 | Kupfer et al. | .............. | 600/431 |
| 5,335,660 A * | 8/1994 | Dumoulin | .............. | 600/419 |
| 6,122,540 A * | 9/2000 | Katzberg et al. | .............. | 600/419 |
| 7,004,904 B2 * | 2/2006 | Chalana et al. | .............. | 600/443 |
| 7,041,059 B2 * | 5/2006 | Chalana et al. | .............. | 600/437 |
| 7,277,807 B2 * | 10/2007 | Dieterle et al. | .............. | 702/76 |
| 7,368,431 B2 * | 5/2008 | Severin et al. | .............. | 514/19.3 |
| 7,550,971 B2 * | 6/2009 | Carpenter et al. | .............. | 324/307 |
| 7,564,245 B2 * | 7/2009 | Lee | .............. | 324/321 |
| 8,134,365 B2 * | 3/2012 | Carpenter et al. | .............. | 324/307 |
| 2008/0046284 A1 * | 2/2008 | Fisher et al. | .............. | 705/2 |
| 2010/0036252 A1 * | 2/2010 | Chalana et al. | .............. | 600/449 |
| 2010/0121220 A1 * | 5/2010 | Nishtala | .............. | 600/581 |

OTHER PUBLICATIONS

Simmons et al., "Dynamic Multi-Planar EPI of the Urinary Bladder During Voiding with Simultaneous Detrusor Pressure Measurement," 1997, Magnetic Resonance Imaging, vol. 15, No. 3, pp. 295-300.*

Cerwinka et al., "Magnetic Resonance Urography in Pediatric Urology," Oct. 25, 2007—available online, Journal of Pediatric Urology, pp. 74-83.*

(Continued)

*Primary Examiner* — James Kish
(74) *Attorney, Agent, or Firm* — Schiff Hardin LLP

(57) ABSTRACT

In a method to determine a kidney function parameter of kidneys of an examination person with the aid of magnetic resonance tomography, at least one magnetic resonance measurement is implemented for an examination region of the examination person that comprises a urinary bladder of the examination person, to acquire magnetic resonance data from the examination region that include at least image data. The concentration of a urophanic substance in the urinary bladder of the examination person is automatically determined based on the acquired magnetic resonance data. A volume of the urinary bladder is automatically determined based on the acquired image data. A kidney function parameter of the kidneys of the examination person is automatically determined on the basis of the determined concentration of the urophanic substance in the urinary bladder and of the specific volume of the urinary bladder.

26 Claims, 4 Drawing Sheets

OTHER PUBLICATIONS

"Magnetic Resonance Cystometry: Accurate Assessment of Bladder Volume With Magnetic Resonance Imaging," Heverhagen, et al., Urology, vol. 60, No. 2 (2002) pp. 309-314.

"Measurement of Glomerular Filtration Rate With Magnetic Resonance Imaging: Principles, Limitations, and Expectations," Grenier, et al., Seminars in Nuclear Medicine, vol. 38 (2008) pp. 47-65.

* cited by examiner

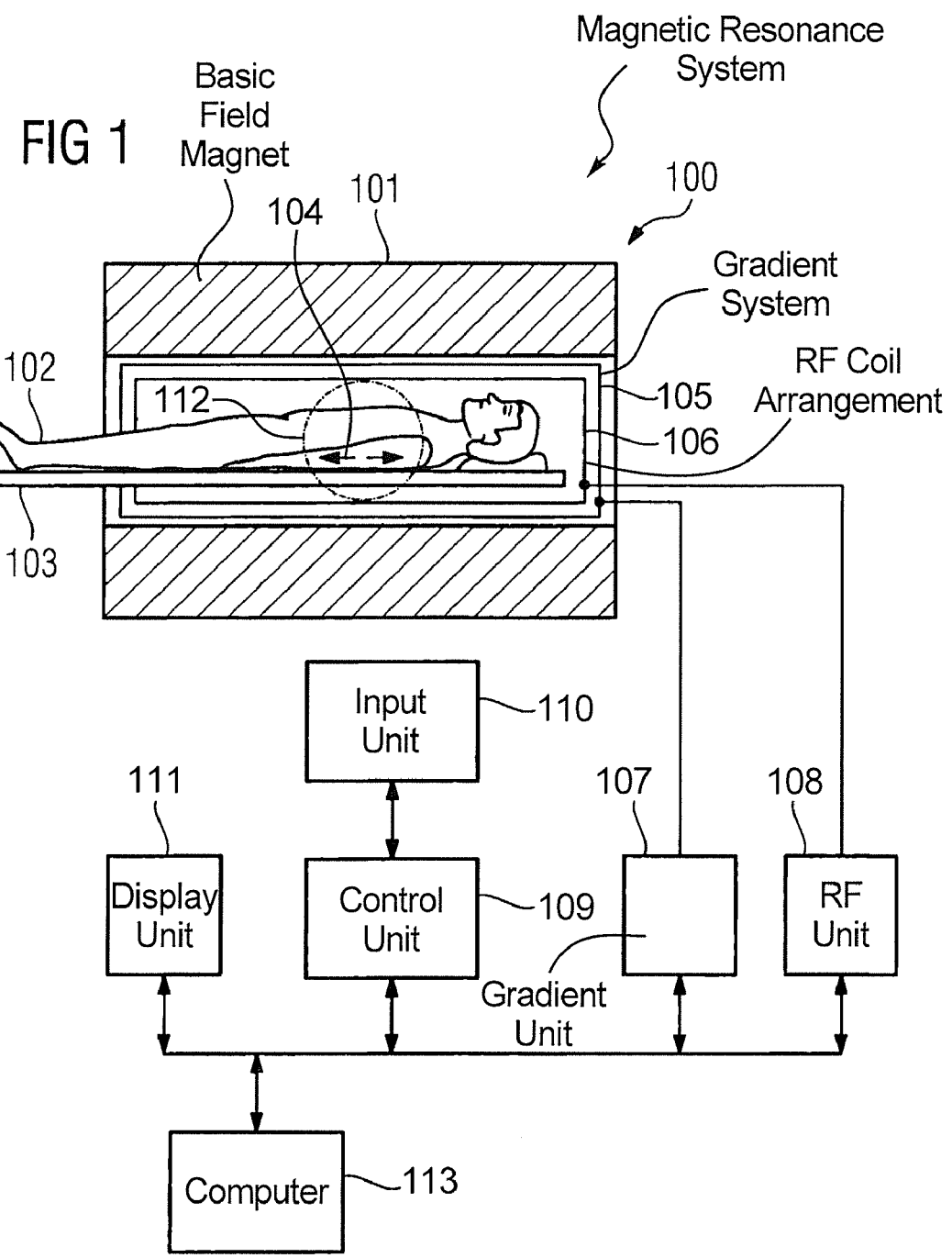

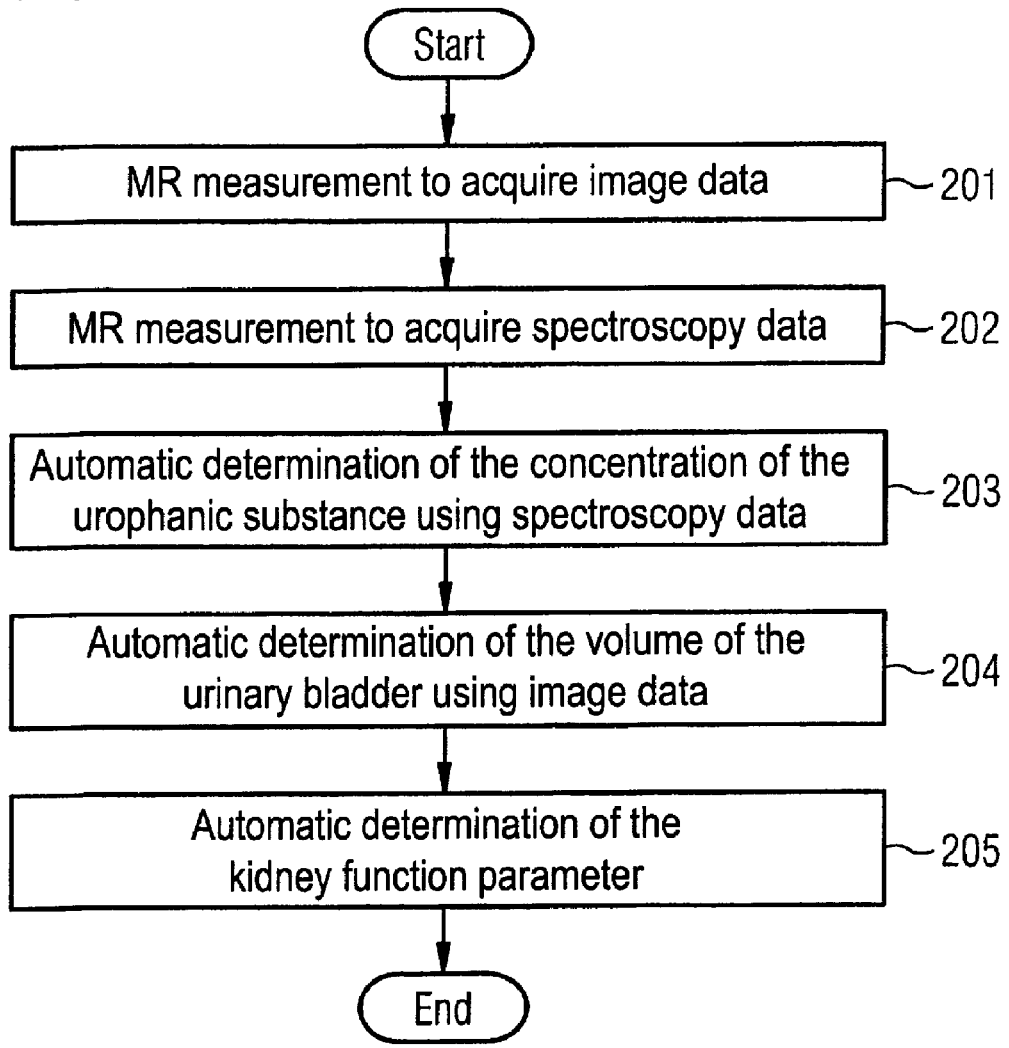

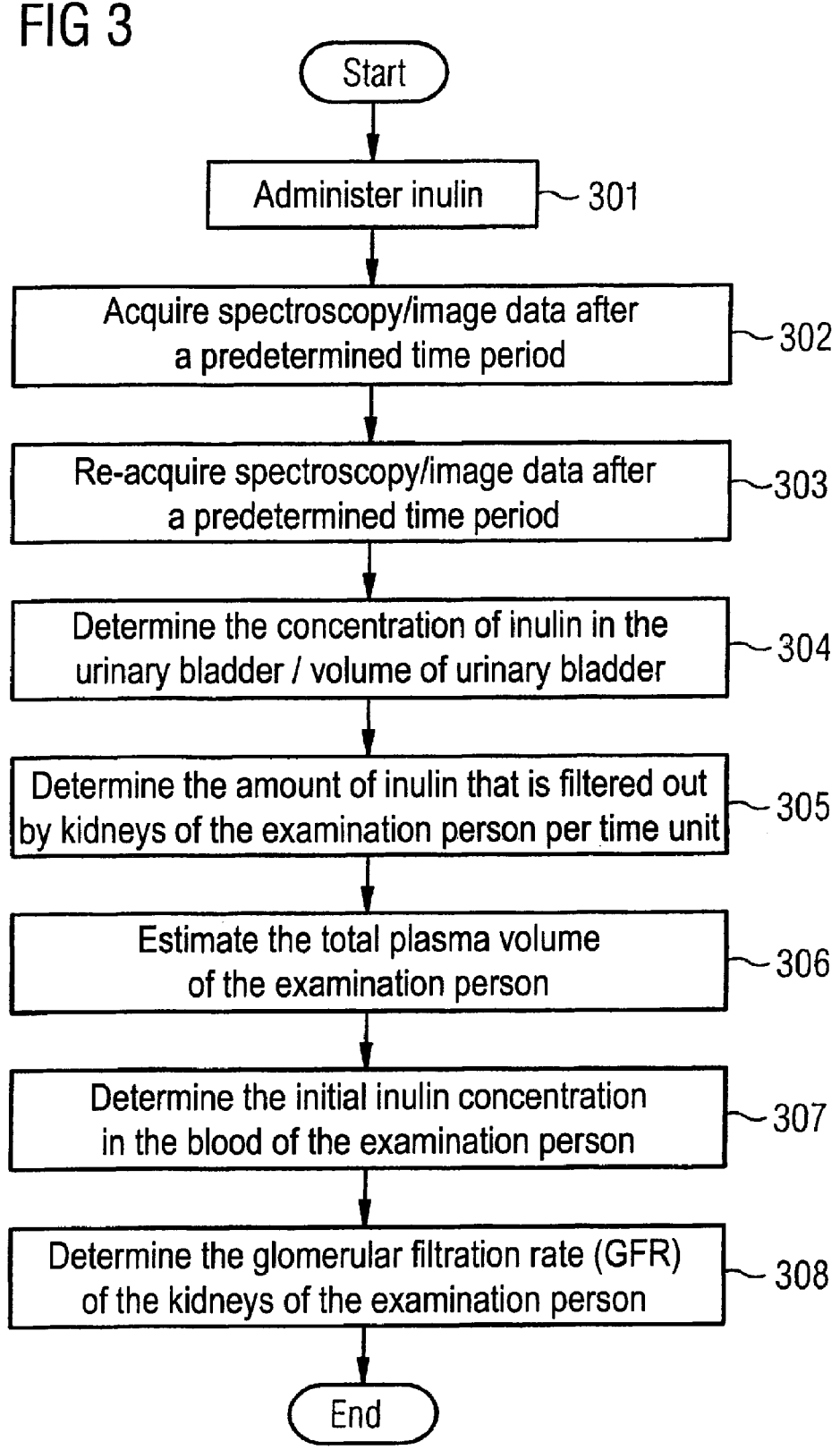

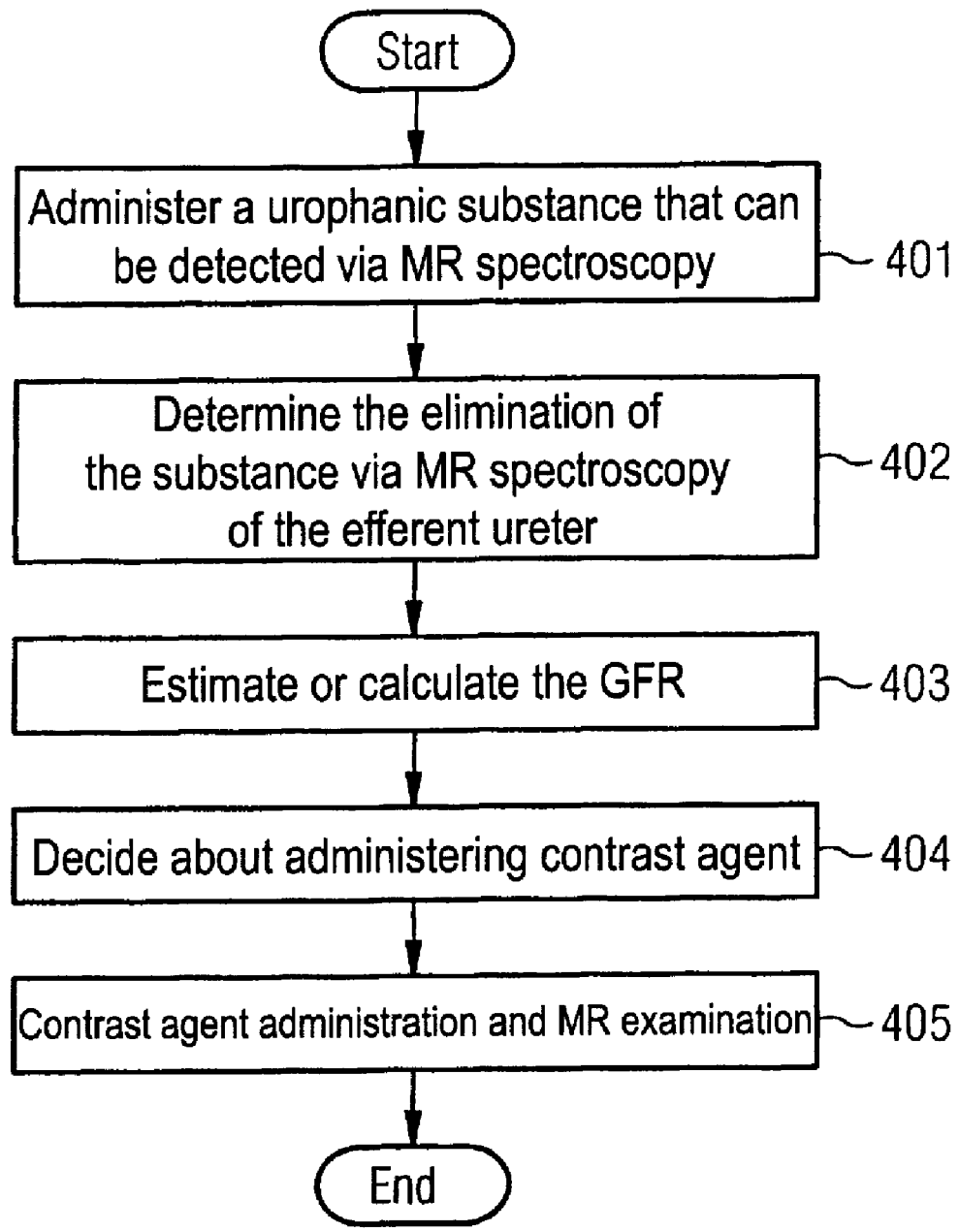

MAGNETIC RESONANCE METHOD AND APPARATUS FOR DETERMINING A KIDNEY FUNCTION PARAMETER

BACKGROUND OF THE INVENTION

1. Field of the Invention

The present invention concerns a method to determine a kidney function parameter of kidneys of an examination subject by magnetic resonance tomography, and a magnetic resonance system for this purpose.

2. Description of the Prior Art

The kidney is an organ that serves to eliminate end products of metabolism. The kidney filters these substances (what are known as urophanic substances) from the blood stream and forms urine which, after intermediate storage in the urinary bladder, is excreted from the body via the urinary tract. Primary urine is filtered from the blood, and valuable plasma components (for example sugar, amino acids and electrolytes) are resorbed into the blood stream. Moreover, a majority of the water filtered out is resorbed, wherein the primary urine is concentrated into secondary (final) urine, which ultimately is conducted via the ureter to the urinary bladder. Parameters that characterize the function of the kidney are, for example, the concentrations of the urophanic substances in the blood or the renal clearance, for example the inulin clearance or the creatinine clearance. Since creatine or inulin are essentially neither secreted nor resorbed, the glomerular filtration rate of the kidneys can be determined from the renal clearance of these substances. Essentially, this indicates the plasma volume from which the urophanic substance has been removed per time unit. The kidney function can thus be characterized with the use of physical quantities.

The determination of these quantities is important for various applications. A determination of the parameters cited above can be useful for scientific studies and for the generation of statistics, for example. Furthermore, databases can be developed that associate a certain glomerular filtration rate with an age or a weight of a person, for example.

Such parameters also can be used in order to establish whether a kidney is operating in its normal parameter range.

Conventional methods to characterize the kidney function use, for example, a determination of the creatinine level in the blood. However, this is very time-consuming since blood must first be extracted from a patient and sent to a laboratory for analysis. The result of the blood test is then generally available only on the next day. Furthermore, the inaccuracy of such a creatinine measurement is disadvantageous. This primarily is due to the fact that the correlation between creatinine level in the blood and the glomerular filtration rate of the kidneys is only indirect across large ranges, such that only a very imprecise determination of the filtration rate is possible. For example, a variation of the glomerular filtration rate only has an effect in the blood as of a change on the order of 50% of the creatinine value.

A further known method uses a Gd-containing contrast agent in order to characterize the kidney function of a patient. The contrast agent is administered to a patient and the excretion of the contrast agent is measured. However, if the patient suffers from a kidney insufficiency, the administration of such a contrast agent is dangerous, in particular since the risk thereby increases of developing a nephrogenic systemic fibrosis. With the establishment of a connection between the administration of contrast agents and the occurrence of an NSF, by now some contrast agents may no longer be administered to patients with limited kidney function.

Consequently, it is desirable to characterize the function of kidneys of an examination person without having to administer an incompatible contrast agent. In particular, it is desirable to conduct a precise characterize in a relatively short time period.

SUMMARY OF THE INVENTION

An object of the present invention is to provide an improved method to determine a parameter characterizing the kidney function.

According to a first aspect of the invention, in a method to determine a kidney function parameter of kidneys of an examination person with the aid of magnetic resonance tomography, at least one magnetic resonance measurement is conducted in an examination region of the examination person that includes the urinary bladder of the examination person, to acquire magnetic resonance data from the examination region that represent at least image data. Based on the acquired magnetic resonance data, the concentration of a urophanic substance in the urinary bladder of the examination person is automatically determined. Furthermore, the volume of the urinary bladder is automatically determined based on the acquired image data. The method furthermore includes an automatic determination of the kidney function parameter of the kidneys of the examination person on the basis of the determined concentration of the urophanic substance in the urinary bladder and of the specific volume of the urinary bladder.

In an embodiment of the method, the magnetic resonance measurement data furthermore include spectroscopic data, and the determination of the concentration of the urophanic substance ensues based on the spectroscopic data. In another embodiment, the determination of the concentration of the urophanic substance can ensue based on the image data. For example, an acquired spectrum can be analyzed to determine the concentration, or intensities in image data can be analyzed.

With such a method, a precise determination of the kidney function parameter can be conducted in a relatively short time period. After acquisition of the magnetic resonance measurement data with the image data, the kidney function parameter can be directly, automatically determined. An administration of a contrast agent is also not necessary for this purpose. The kidney function parameter can subsequently be stored in a database, for example, or be provided immediately for the implementation of an additional method.

In another embodiment of the method according to the invention, the at least one magnetic resonance measurement includes a magnetic resonance spectroscopy measurement to acquire spectroscopic data, and an imaging magnetic resonance measurement to acquire image data. The spectroscopic data thus do not have to be spatially resolved, in contrast to which the imaging magnetic resonance measurement enables a high-resolution imaging of the urinary bladder.

The urophanic substance is, for example, inulin. The urophanic substance can be introduced into the blood stream of the examination person at a predetermined time before the implementation of the at least one magnetic resonance measurement. The predetermined time then can be used for the determination of the kidney function parameter. For example, the quantity of the urophanic substance that is filtered out by the kidneys per time unit can be determined based on the specific concentration of the urophanic substance in the urinary bladder and the determined volume of the urinary bladder. This quantity already represents a parameter characterizing the kidney function.

According to one embodiment of the present invention, the kidney function parameter is a glomerular filtration rate of the kidneys of the examination person. The glomerular filtration rate can thereby be determined with various methods. For example, an association of a glomerular filtration rate with the determined quantity of urophanic substance filtered out per time unit ensues using a calibration curve that, for example, was created on the basis of historical data. The glomerular filtration rate can thus be directly concluded with the determination of the amount of the substance that is filtered out per time unit. The calibration curve can be created via similar measurements with the aid of test subjects, for example.

According to a further embodiment, the determination of the glomerular filtration rate ensues in that an estimation of the total plasma volume of the examination person is initially conducted. Based on the total plasma volume and a quantity of the urophanic substance that was introduced into the blood stream of the examination person, a concentration of the urophanic substance in the blood plasma of the examination person is subsequently determined. The glomerular filtration rate can subsequently be determined based on the determined quantity of urophanic substance filtered out per time unit and the concentration of the urophanic substance in the blood plasma. The glomerular filtration rate can thereby be determined with a high precision.

A further increase in the precision can be achieved what, for example, the overall magnetic resonance measurement is composed multiple magnetic resonance measurements for a repeated acquisition of magnetic resonance measurement data at predetermined time intervals. The determination of the kidney function parameter then ensues on the basis of the magnetic resonance measurement data acquired at predetermined time intervals.

Additional parameters can also be used for the determination of the kidney function parameter, for example a magnetic resonance-spectroscopically determined concentration of the urophanic substance in the tissue of the examination person, a cardiac output of the examination person or a blood flow in a renal artery of the examination person. The precision of the determination of the kidney function parameter can thereby possibly be additionally increased.

According to a further embodiment of the method according to the invention, the concentration of the urophanic substance in the urinary bladder is determined based on characteristic spectral properties of the urophanic substance in the acquired spectroscopic data. The urophanic substance can also be marked with a marker atom, wherein the concentration of the urophanic substance in the urinary bladder can then be determined on the basis of characteristic spectral properties of the marker atom in spectroscopic data that comprise the acquired magnetic resonance measurement data or on the basis of intensities in the image data that are caused by marker atoms. The precision of the concentration determination can be increased with the aid of a marker atom. For example, the concentration can be determined using a comparison value. For this the at least one magnetic resonance measurement includes an acquisition of magnetic resonance measurement data of a phantom, wherein the phantom contains the urophanic substance in a predetermined concentration. The determination of the concentration of the urophanic substance in the urinary bladder can then ensue using the magnetic resonance measurement data from the examination region and the magnetic resonance measurement data of the phantom.

If the acquired magnetic resonance measurement data include spectroscopic data for concentration determination, a calibration of the spectroscopic data with the spectroscopic data acquired from the phantom can thus ensue. If, on the other hand, the concentration is determined on the basis of the image data, the intensities in the acquired image data can be calibrated on the basis of the image data acquired by the phantom. In both cases, the acquisition of magnetic resonance measurement data of the phantom thus enables an improvement of the concentration determination.

For the determination of the volume of the urinary bladder, a segmentation of the urinary bladder in the image data is implemented, for example. The image data can be acquired during an imaging measurement that is configured for a selective depiction of the urinary bladder volume, for example. Such an imaging measurement can be a T2-weighted measurement, for example. The urinary bladder (which essentially contains water) can appear very bright in a proton image with strong contrast, whereby an automatic segmentation of the urinary bladder is enabled. A high contrast of the urinary bladder can also be achieved via marking of the urophanic substance with a marker atom, wherein the at least one magnetic resonance measurement then includes an imaging measurement that is configured for the selective depiction of the marker atom. For example, inulin can be marked with 13C, which can then be selectively shown in a carbon measurement.

According to a further embodiment, the urophanic substance is one of the metabolites of the examination person's own body. The urophanic substance can be creatinine, for example. A determination of the kidney function parameter can thus ensue without a urophanic substance having to be previously introduced into the blood stream of the examination person.

According to a further embodiment, a determination of whether a limitation of the kidney function exists furthermore ensues using the determined kidney function parameter of the kidneys of the examination person. For example, this can ensue automatically by comparison with kidney function parameters stored in a database. It can therefore be established whether the determined kidney function lies inside a parameter range of normal kidney function or outside of this parameter range.

Furthermore, an establishment of whether a contrast agent for a subsequent magnetic resonance tomography examination may be administered to the examination person can ensue on the basis of the determined kidney function parameter of the kidneys of the examination person. For example, given a limited kidney function an administration of such a contrast agent can be disadvantageous; in particular, it can lead to a nephrogenic systemic fibrosis. Such an establishment is thus advantageous since a contrast agent administration can be prevented given an existing limited kidney function. Furthermore, the kidney function parameter can be determined with relatively high precision immediately before an implementation of the magnetic resonance tomography examination, which was not possible with conventional methods as explained in the preceding. The determination of whether a contrast agent may be administered can ensue automatically, for example again by comparison of the determined kidney function parameter with values that are stored in a database.

According to a further aspect of the present invention, a magnetic resonance system is provided for a determination of a kidney function parameters of kidneys of an examination person. The magnetic resonance system has an acquisition unit that is designed to implement magnetic resonance measurements in an examination region of an examination person. Furthermore, a control unit is provided that controls the acquisition unit such that magnetic resonance measurement data that include at least image data are acquired in at least one magnetic resonance measurement from an examination region of the examination person, the image data representing the urinary bladder of the examination person. Furthermore, the magnetic resonance system has a computer that automatically determines the concentration of a urophanic substance in the urinary bladder of the examination person on the basis of the acquired magnetic resonance measurement data as well as a volume of the urinary bladder based on the acquired image data. Furthermore, the computer implements an automatic determination of the kidney function parameter of the kidneys of the examination person based on the determined concentration of the urophanic substance in the urinary bladder and on the determined volume of the urinary bladder. The advantages cited in the preceding with regard to the method according to the invention can likewise be achieved with the magnetic resonance system according to the invention.

In an embodiment, the magnetic resonance system is designed to operate according to one of the methods cited in the preceding.

The invention furthermore concerns a computer-readable medium encoded with programming instructions that cause the method described above to be executed by a computer system. The computer-readable medium can be used, for example, in a computer system functionally connected with a conventional magnetic resonance system.

BRIEF DESCRIPTION OF THE DRAWINGS

FIG. 1 schematically shows a magnetic resonance system for a determination of a kidney function parameter according to an embodiment of the present invention.

FIG. 2 is a flowchart of an embodiment of a method according to the invention.

FIG. 3 is a flowchart of a further embodiment of the method according to the invention.

FIG. 4 is a flowchart of a further embodiment of the method according to the invention.

DESCRIPTION OF THE PREFERRED EMBODIMENTS

In the following, the invention is described in detail using embodiments in which both spectroscopic data and image data are acquired to determine the kidney function parameter. However, it should be clear that the described embodiments can likewise be realized without the acquisition of spectroscopic data, for example, the concentration of the urophanic substance being determined using acquired image data. The explanations provided in the following thus can also be applied to other embodiments in which an acquisition of spectroscopic data does not ensue.

FIG. 1 schematically shows an embodiment of a magnetic resonance (MR) system according to the invention. The magnetic resonance system is designed for a simple determination of a kidney function parameter via implementation and evaluation of magnetic resonance measurements. Such an MR system has a basic field magnet 101 that generates a polarization field B0. An examination person 102 on a bed 103 is slid into the magnet, as is schematically represented by the arrows 104. The MR system 100 furthermore possesses a gradient system 105 to generate magnetic field gradients that are used for imaging and spatial coding. To excite the polarization resulting in the basic magnetic field, a radio-frequency (RF) coil arrangement 106 is provided that radiates a radio-frequency field into the examined person 102 in order to deflect the magnetization from the equilibrium state. To control the magnetic field gradients, a gradient unit 107 is provided, and an RF unit 108 is provided to control the radiated radio-frequency pulses. A control unit 109 centrally controls the magnetic resonance system; the selection of imaging sequences likewise ensues in the control unit 109. Via an input unit 110, an operator can select a sequence protocol and input and modify imaging parameters that are displayed on a display 111. Control unit 109 can furthermore control the implementation of a magnetic resonance spectroscopy measurement with the magnetic resonance system 100. The magnetic resonance system 100 is thus suitable both for the acquisition of image data from an examination region 112 of the examination person 102 and for the acquisition of spectroscopic data. Magnetic resonance signals acquired from the examination region 112 are subsequently evaluated in computer 113. The computer 113 can thereby implement both calculations to evaluate spectroscopic data and a reconstruction of acquired image data.

The general functionality of an MR system is known to those skilled in the art, so a more detailed description of the general components is not necessary.

The MR system shown in FIG. 1 is configured for the determination of a kidney function parameter of kidneys of the examination person 102. Control unit 109 thereby initiates the acquisition of both image data and spectroscopic data from the examination region 112. These are acquired with the aid of the acquisition unit (which comprises, for example, magnet 101, gradient system 105, radio-frequency coil arrangement 106, gradient unit 107 and RF unit 108) during one or more magnetic resonance measurements. To determine the kidney function parameter, the acquired spectroscopy and image data are subsequently evaluated in computer 113. Computer 113 is designed for automatic implementation of a segmentation of the image data to determine the volume of the urinary bladder of the examination person as well as to analyze the spectroscopic data to determine the concentration of an urophanic substance in the urinary bladder of the examination person. Computer 113 can furthermore comprise a database to store historical values of kidney function parameters, for example to generate a calibration curve. Using the magnetic resonance measurement, specific kidney function parameters can also be stored in computer 113 for a later use.

To acquire the spectroscopic data, control unit 109 initiates (for example) the implementation of a magnetic resonance spectroscopic method with the magnetic resonance system 100. for example, a spectroscopic imaging method such as chemical shift imaging (CSI) can be implemented, or a single volume technique in which a spectrum of a target volume, is acquired in the examination region 112. The excitation of a target volume can ensue via successive, selective excitation of three orthogonal layers, for example. For example, a secondary spin echo is then acquired from the excited target volume, wherein the spectrum can be obtained via Fourier transformation of the acquired signal. In the spectrum, different resonances that are caused by substances present in the target volume can subsequently be identified in the spectrum. For example, the concentration of the associated substance in the target volume can be determined via evaluation of an area below a resonance in the spectrum. Given a spectroscopic imaging method, this can also ensue with spatial resolution. For example, after a non-selective 90° radio-frequency pulse a combination of magnetic field gradients can be switched in three spatial directions in order to implement a phase coding in three dimensions. The magnetic resonance signal can then be read out in the absence of any gradients. Repetition of the sequence with a variation of the field gradients yields the desired spatial resolution.

The magnetic resonance measurement to acquire the image data can include, for example, a $T_2$-weighted spin echo sequence. To show the fluid located in the bladder of the examination person with high contrast, long TR and TE times are used for this, for example. Spin echo sequences to generate proton images in which fluid is shown with high contrast are known to those skilled in the art and therefore need not be explained in detail herein. Naturally, other magnetic resonance sequences can also be used as long as the volume of the urinary bladder of the examination person can be at least approximately determined from the acquired image data. In particular, image data from only a single slice can also be acquired, wherein an estimation of the volume of the urinary bladder can then ensue based on a model such as a sphere or a spheroid.

The flowchart in FIG. 2 can be illustrated in an example of an embodiment of the method according to the invention. This method can be implemented fully automatically with the MR system 100 shown in FIG. 1. A magnetic resonance measurement to acquire image data thereby ensues in Step 201 and a magnetic resonance measurement to acquire spectroscopic data ensues in Step 202. The image data and the spectroscopic data are acquired from a region of the examination person that contains the urinary bladder of the examination person. The implementation of these MR measurements is controlled by control unit 109. The acquired data are subsequently evaluated in computer 113. An automatic determination of the concentration of a urophanic substance that the urinary bladder of the examination person contains thereby ensues in Step 203 using the spectroscopic data. The determination of the concentration can ensue via association of peaks in the spectrum with specific substances and via estimation of the area under the peaks in the spectrum, for example. The peaks in the spectrum can be identified using their characteristic resonance frequencies, wherein a concentration determination is enabled through preceding calibration measurements, for example.

As was previously mentioned, Step 202 is optional, and the determination of the concentration can likewise ensue using the acquired image data. This is particularly advantageous if the urophanic substance is marked with a marker atom so that the image data significantly depict the urophanic substance. The intensity of the acquired magnetic resonance signal, and thus the intensity if an image data point, then depends on the concentration of the urophanic substance at the location of the pixel. In such an embodiment of the method, the concentration can thus be determined with the use of image processing in Step 203, wherein a calibration measurement on a phantom to calibrate the intensities can be used as necessary.

An automatic determination of the volume of the urinary bladder using the image data ensues in Step 204. For example, a segmentation of the urinary bladder can ensue here in one or more slice images. Generally known segmentation algorithms can be used for this, for example an "edge detection" algorithm. The urinary bladder can be segmented in a three-dimensional image data set for volume determination; however, as mentioned, an estimation of the volume with a single slice image using a model is also possible.

With the calculated concentration of the urophanic substance in the urinary bladder and the estimated volume of the urinary bladder, in Step 205 a kidney function parameter can now be automatically determined. For example, the quantity of the urophanic substance in the urinary bladder can be determined, and with this also the excreted quantity of the urophanic substance per time period if necessary. A kidney function parameter (for example a renal clearance, in particular a glomerular filtration rate (GFR)) can also be determined.

With the described method, the determination can ensue fully automatically in a relatively short time and with a relatively high precision. Furthermore, the kidney function parameter can be determined without administering contrast agent. The determined kidney function parameter can be additionally processed in computer 113; however, it can also be presented at display 111 or can be stored in a database for a later use.

FIG. 3 shows a flow diagram of a further embodiment of the method according to the invention. In this embodiment, inulin is used as a urophanic substance. Before the implementation of the actual method, inulin is thereby first administered (for example intravenously) to an examination person in Step 301. The examination person is subsequently placed on the patient bed of the magnetic resonance system after a predetermined time (for example 30 minutes) and an acquisition of spectroscopic and image data is conducted as described in the preceding (Step 302). During the predetermined time period, the kidney has already filtered out a portion of the inulin from the blood stream of the examination person, wherein this is initially stored in the urinary bladder before excretion. Via continuing filtration of the blood by the kidneys, an increase of the concentration of the inulin in the urinary bladder of the examination person thereby ensues with time. In order to improve the precision of the determination of the kidney function parameter, a new acquisition of spectroscopic and image data ensues again in a next Step 303 after a predetermined time period, for example 35 or 40 minutes after administration of the inulin in Step 301. Depending on the application, additional Steps can follow in which spectroscopy and/or image data are acquired.

The concentration of inulin in the urinary bladder of the examination person as well as the volume of the urinary bladder are now determined in Step 304 as described in the preceding. An improvement of the precision of the concentration determination can be obtained via marking of the inulin with 13C, for example. The one or multiple magnetic resonance measurements to acquire the image and spectroscopic data can be implemented with a dedicated 13C excitation, for example. Inulin can therefore be shown with a high contrast; an identification of the inulin in the acquired spectrum as well as a determination of the inulin concentration in the urinary bladder is likewise simplified. If the image data are likewise acquired during a carbon MR measurement, the depiction of the urinary bladder thus ensues with high contrast due to the 13C present in it, which in turn simplifies a segmentation and volume determination. To achieve a high precision of the concentration determination, the MR measurement can furthermore be implemented in parallel at the urinary bladder of the examination person and at a phantom. The phantom is, for example, a sample bottle that contains the urophanic substance (here 13C-marked inulin) in a predetermined concentration. Via acquisition of the MR spectrum of the phantom, the spectrum acquired from the urinary bladder of the examination person can be calibrated and a precise concentration determination of the 13C-marked inulin in the urinary bladder can consequently be implemented.

In the present exemplary embodiment, the glomerular filtration rate (GFR) of the kidneys should be determined as a kidney function parameter. For this the determination of the amount of inulin that is filtered out by the kidneys of the examination person per time unit initially ensues in Step 305. Since the time interval between inulin administration and acquisition of the spectroscopy and image data is known, and the amount of inulin in the urinary bladder can be calculated on the basis of the urinary bladder volume and the concentration of inulin in the urinary bladder, the determination in Step 305 can be implemented in a simple manner. In particular, the precision for this determination can additionally be increased by the use of the additionally acquired spectroscopic data and image data (Step 303).

An estimation of the total plasma volume of the examination person ensues in Step 306. The blood volume can, for example, be estimated using height, weight, age or additional properties of the examination person. Since the amount of inulin that was administered to the examination person (Step 301) is known, in Step 307 the initial inulin concentration in the blood of the examination person can furthermore be determined. In Step 308 the glomerular filtration rate of the kidneys of the examination person can be determined via division of the excreted inulin quantity determined in Step 305 by the plasma concentration of the inulin. This determination can, for example, also be implemented for the multiple MR measurements (Step 303), for example, by determining a glomerular filtration rate with higher precision by averaging. Other methods to determine the GFR can also be used that are based on the acquired spectroscopic data and image data. For example, a calibration curve generated in advance with test subjects can be used in order to convert the inulin amount excreted per time unit (calculated in Step 305) into the GFR. Naturally, the excreted inulin quantity per time can also be directly specified as a kidney function parameter.

An additional increase of the precision can be achieved in that additional parameters (that can be determined in the MR system, for example) are included in the calculation. For this, for example, a spectroscopically determined concentration of the urophanic substance in the tissue, a cardiac output of the examination person or a blood flow in a renal artery of the examination person (renal plasma flow) can be used. An acquisition of the urophanic substance in the tissue reduces the concentration of the substance in blood plasma, for example, which affects the concentration of the substance measured in the urinary bladder. The cardiac output of the examination person is the blood flow in the aorta of the examination person; this can likewise affect the determination of a kidney function parameter.

A number of additional embodiments and modifications of the invention described in the preceding can be implemented. For example, the body's own metabolites (for example creatinine) can be measured instead of externally supplied urophanic substances. The urophanic substance can also be measured without marking (by 13C, for example) or using other markers. As mentioned in the preceding, unmarked, externally supplied substances such as inulin can be measured using characteristic properties of their spectrum. A selection presentation of the urinary bladder can also be achieved not only via measurement of 13C (which can be used to mark the inulin) but also via acquisition of the image data set with predetermined imaging parameters.

FIG. 4 shows a flowchart of a further embodiment of the method according to the invention. In this embodiment, the method according to the invention is implemented before the implementation of a contrast agent-enhanced MR examination. A urophanic substance that can be detected via MR spectroscopy is administered to the person to be examined in a first Step 401. In Step 402, the elimination of the substance by the kidneys is determined via MR spectroscopy of the efferent ureter. This can ensue according to any of the methods described in the preceding. An estimation or calculation of the glomerular filtration rate of the kidneys of the examination person ensues in Step 403. Using the GFR, it can be determined whether the kidney function of the examination person is limited. This determination can, for example, ensue via comparison of the GFR with values that correspond to a normal kidney function. In a next Step 404, it is established whether a contrast agent can be administered to the examination person. If the subject has limited kidney function, for example, an administration of specific contrast agents is not permitted. For example, it can be determined in Step 404 that an administration of MR contrast agent is permitted if the GFR estimated in. Step 403 lies within a predetermined GFR range. Step 404 can thus likewise be implemented automatically, for example with a computer. If it was established in Step 404 that contrast agent can be administered, the contrast agent administration and a subsequent contrast agent-assisted MR examination ensue in Step 405. If no contrast agent may be administered, Step 405 is not implemented.

The embodiment of the method according to the invention that is described in relation to FIG. 4 in particular has advantages in view of the fact that, since the discovery of a connection between the administration of MR contrast agent and the disease nephrogenic systemic fibrosis (NSF), some MR contrast agents may no longer be administered to examination persons with limited kidney function. When a contrast agent-assisted MR examination is to be conducted, however, the limitation of the kidney function is often not known at the point in time of the examination. With the described method, it can be established before a contrast agent administration whether a limitation of the kidney function exists. A limitation of the kidney function can be directly determined with the available means, i.e. with the MR system. Furthermore, the determination can ensue in a relatively short amount of time without having to first wait for laboratory values. With the determination of whether a limitation of the kidney function exists, a decision can therefore be immediately made as to whether a contrast agent may be administered. This decision can even be made automatically if necessary.

Naturally, the features of the embodiments described in the preceding can be combined. For example, in the method from FIG. 2 an injection of a urophanic substance can also ensue as well as an implementation of additional MR measurements to increase the precision. In the method illustrated using FIG. 3, the acquisition of spectroscopic data can also be omitted and the concentration determination can ensue based on the image data. This is in particular advantageous if this type of concentration determination is combined with a 13C-marking of the inulin.

In summary, a precise and fast method to automatically determine a kidney function parameter is achieved with the present invention. The method is advantageous because it requires no contrast agent administration. Furthermore, efforts on the part of operators of the MR system are reduced in the case of an automatic implementation.

Although modifications and changes may be suggested by those skilled in the art, it is the intention of the inventors to embody within the patent warranted hereon all changes and modifications as reasonably and properly come within the scope of their contribution to the art.

We claim as our invention:
1. A method to determine a kidney function parameter of kidneys of an examination subject by magnetic resonance tomography, comprising the steps of:
   placing an examination subject in a magnetic resonance data acquisition unit with the urinary bladder of the examination subject located in an examination volume of the magnetic resonance data acquisition unit;
   with said magnetic resonance data acquisition unit, implementing at least one magnetic resonance data acquisition procedure to acquire magnetic resonance data from the examination volume, that comprise at least image data;

using a processor to automatically determine a concentration of a urophanic substance in the urinary bladder of the examination subject from the acquired magnetic resonance data;

using said processor to automatically determine a volume of the urinary bladder from the image data; and using said processor to automatically determine a kidney function parameter of kidneys of the examination subject from the determined concentration of the urophanic substance in the urinary bladder and the determined volume of the urinary bladder.

2. A method as claimed in claim 1 comprising implementing said at least one magnetic resonance data acquisition procedure to also acquire spectroscopic data in said magnetic resonance data and, using said processor to determine the concentration of the urophanic substance from said spectroscopic data.

3. A method as claimed in claim 2 comprising implementing said at least one magnetic resonance data acquisition procedure as a combination of a magnetic resonance spectroscopy measurement and a magnetic resonance imaging measurement.

4. A method as claimed in claim 1 comprising, using said processor to determine said concentration of said urophanic substance in the urinary bladder from said image data.

5. A method as claimed in claim 1 comprising determining a concentration of inulin as said urophanic substance.

6. A method as claimed in claim 1 comprising artificially introducing the urophanic substance into the bloodstream of the examination subject at a predetermined time before implementing said at least one magnetic resonance data acquisition procedure.

7. A method as claimed in claim 6 comprising using said processor to additionally use said predetermined time to determine said kidney function parameter.

8. A method as claimed in claim 1 comprising determining a concentration of a metabolite in the body of the examination subject as said urophanic substance.

9. A method as claimed in claim 8 comprising determining a concentration of creatinine as said metabolite.

10. A method as claimed in claim 1 comprising implementing said at least one magnetic resonance data acquisition procedure to also acquire spectroscopic data among said magnetic resonance data and in using said processor to determine the concentration of the urophanic substance in the urinary bladder dependent on characteristic spectral properties of the urophanic substance represented in the spectroscopic data.

11. A method as claimed in claim 1 comprising artificially marking the urophanic substance in the examination subject with a marker atom, and implementing said at least one magnetic resonance data acquisition procedure to also acquire spectroscopic data among said magnetic resonance data and using said processor to determine said concentration of urophanic substance in the urinary bladder from characteristic spectral properties of said marker atom as represented in said spectroscopic data.

12. A method as claimed in claim 1 comprising artificially marking said urophanic substance in the urinary bladder with a marker atom and, using said processor to determine the concentration of the urophanic substance in the urinary bladder from intensities in the image data produced by marker atoms.

13. A method as claimed in claim 1 comprising placing a phantom in said examination volume, said phantom containing said urophanic substance in a predetermined concentration, and including, in said at least one magnetic resonance data acquisition procedure, acquisition of magnetic resonance data from said phantom and using said processor to determine the concentration of the urophanic substance in the urinary bladder using the magnetic resonance data acquired from the examination subject and the magnetic resonance data acquired from the phantom.

14. A method as claimed in claim 1 comprising, using said processor to determine the volume of the urinary bladder by segmenting the urinary bladder in said image data.

15. A method as claimed in claim 1 comprising implementing said at least one magnetic resonance data acquisition procedure using an imaging sequence that acquires, as said image data, data that selectively depict the Volume of the urinary bladder.

16. A method as claimed in claim 1 comprising artificially administering a marker atom to said urophanic substance in the examination subject, and implementing said at least one magnetic resonance data acquisition procedure using an imaging sequence that acquires, as said image data, data that selectively depicts said marker atom.

17. A method as claimed in claim 1 comprising, using said processor to determine said kidney function parameter by determining an amount of said urophanic substance that is filtered out by the kidneys per time unit, from the determined concentration of the urophanic substance in the urinary bladder and the determined volume of the urinary bladder.

18. A method as claimed in claim 17 comprising generating a calibration curve based on historical data from the examination subject that correlates a glomerular filtration rate with the quantity of urophanic substance filtered out per time unit, and, using said processor to determine said glomerular filtration rate as said kidney function parameter by correlating a glomerular filtration rate in said calibration curve with the determined amount of urophanic substance filtered out by the kidneys per time unit.

19. A method as claimed in claim 17 comprising:

providing said processor with an estimation of a total plasma volume of the examination subject;

using said processor to determine a concentration of the urophanic substance in the plasma of the examination subject from the total plasma volume and a quantity of the urophanic substance introduced into the blood stream of the examination subject; and determining a glomerular filtration rate, as said kidney function parameter, of the kidneys of the examination subject from the determined quantity of urophanic substance filtered out of the kidneys per time unit and the determined concentration of the urophanic substance in the blood plasma.

20. A method as claimed in claim 1 comprising determining a glomerular filtration rate of the kidneys of the examination subject as said kidney function parameter.

21. A method as claimed in claim 1 comprising implementing said at least one magnetic resonance data acquisition procedure as a plurality of repeated magnetic resonance data acquisitions, respectively repeated at predetermined time intervals and comprising, using said processor to determine said kidney function parameter from magnetic resonance measurement data acquired at said predetermined time intervals.

22. A method as claimed in claim 1 comprising, using said processor to determine said kidney function parameter dependent on additional information selected from the group consisting of a magnetic resonance-spectroscopically determined concentration of the urophanic substance in tissue of the examination subject, cardiac output of the examination subject, and blood flow in a renal artery of the examination subject.

23. A method as claimed in claim 1 comprising using said kidney function parameter from the output of the processor to identify whether an abnormality of the kidney function of the examination subject exists.

24. A method as claimed in claim 1 comprising determining whether a contrast agent for a subsequent magnetic resonance tomography examination, following said at least one magnetic resonance data acquisition procedure, may be safely administered to the examination subject dependent on the kidney function parameter at the output of said processor.

25. A magnetic resonance system comprising:
- a magnetic resonance data acquisition unit having an examination volume;
- a control unit configured to operate said magnetic resonance data acquisition unit to implement at least one magnetic resonance data acquisition procedure to acquire magnetic resonance data from an examination subject having a urinary bladder in the examination volume, said magnetic resonance data comprising at least image data;
- a processor configured to automatically determine a concentration of a urophanic substance in the urinary bladder of the examination subject from the acquired magnetic resonance data;
- said processor being configured to automatically determine a volume of the urinary bladder from the image data; and
- said processor being configured to automatically determine a kidney function parameter of kidneys of the examination subject from the determined concentration of the urophanic substance in the urinary bladder and the determined volume of the urinary bladder.

26. A non-transitory computer-readable medium encoded with programming instructions to determine a kidney function parameter of kidneys of an examination subject in a magnetic resonance data acquisition unit with the urinary bladder of the examination subject located in an examination volume of the magnetic resonance data acquisition unit, said programming instructions causing a computer system associated with the magnetic resonance data acquisition unit to:
- operate said magnetic resonance data acquisition unit to implement at least one magnetic resonance data acquisition procedure to acquire magnetic resonance data from the examination volume, that comprise at least image data;
- automatically determine a concentration of a urophanic substance in the urinary bladder of the examination subject from the acquired magnetic resonance data;
- automatically determine a volume of the urinary bladder from the image data; and
- automatically determine a kidney function parameter of kidneys of the examination subject from the determined concentration of the urophanic substance in the urinary bladder and the determined volume of the urinary bladder.

* * * * *